(12) United States Patent
Manninen et al.

(10) Patent No.: US 9,000,043 B2
(45) Date of Patent: Apr. 7, 2015

(54) PHENOXYETHOXY COMPOUNDS

(71) Applicant: Eli Lilly and Company, Indianapolis, IN (US)

(72) Inventors: Peter Rudolph Manninen, Brownsburg, IN (US); Alan M Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/171,817

(22) Filed: Feb. 4, 2014

(65) Prior Publication Data
US 2014/0235718 A1      Aug. 21, 2014

Related U.S. Application Data

(60) Provisional application No. 61/765,057, filed on Feb. 15, 2013.

(51) Int. Cl.
*C07C 235/34* (2006.01)
*C07C 235/06* (2006.01)

(52) U.S. Cl.
CPC .............. *C07C 235/34* (2013.01); *C07C 235/06* (2013.01)

(58) Field of Classification Search
CPC ...................................................... C07C 35/34
See application file for complete search history.

(56) References Cited

U.S. PATENT DOCUMENTS

2005/0250818 A1    11/2005    Koike et al.

FOREIGN PATENT DOCUMENTS

| WO | 2005021508 A1 | 3/2005 |
| WO | 2011102149 A1 | 8/2011 |

*Primary Examiner* — James D Anderson
(74) *Attorney, Agent, or Firm* — Nelsen L. Lentz

(57) ABSTRACT

The present invention provides a compound of the Formula I:

Formula I

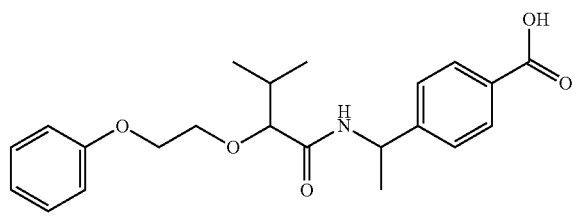

or a pharmaceutically acceptable salt thereof.

8 Claims, No Drawings

PHENOXYETHOXY COMPOUNDS

The present invention relates to novel phenoxyethoxy compounds, to pharmaceutical compositions comprising the compounds, to methods of using the compounds to treat physiological disorders, and to intermediates and processes useful in the synthesis of the compounds.

The present invention is in the field of treatment of inflammatory conditions, such as arthritis, including osteoarthritis and rheumatoid arthritis, and further including pain associated with these conditions. Arthritis affects millions of patients in the United States alone and is a leading cause of disability. Treatments often include NSAIDs (nonsteroidal anti-inflammatory drugs) or COX-2 inhibitors, which may produce untoward cardiovascular and/or gastrointestinal side effects. As such, patients who have a poor cardiovascular profile, such as hypertension, may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3 and EP4. It has been disclosed that EP4 is the primary receptor involved in joint inflammatory pain in rodent models of rheumatoid arthritis and osteoarthritis (See, for example, *J. Pharmacol. Exp. Ther.*, 325, 425 (2008)). Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors. (See, for example, *Bioorganic & Medicinal Chemistry Letters*, 21, 484 (2011)).

US 2005/0250818 discloses certain ortho substituted aryl and heteroaryl amide compounds that are EP4 receptor selective antagonists with analgesic activity. In addition, WO 2011/102149 discloses certain compounds that are selective EP4 antagonists which are useful in treating IL-23 mediated diseases.

The present invention provides certain novel compounds that are selective inhibitors of EP4 relative to EP1, EP2, and EP3. In addition, the present invention provides certain novel compounds with the potential for reduced cardiovascular or gastrointestinal side effects in comparison to traditional NSAIDs.

Accordingly, the present invention provides a compound of the Formula I:

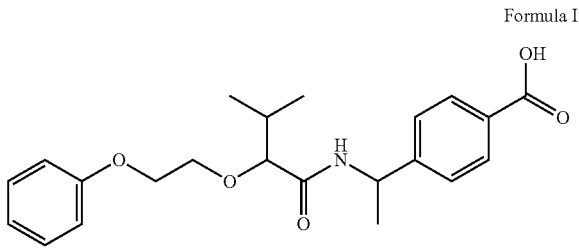 [SMILES: CC(NC(=O)C(OCCOc1ccccc1)C(C)C)c1ccc(C(=O)O)cc1]

Formula I or a pharmaceutically acceptable salt thereof.

The present invention also provides a method of treating arthritis in a patient, comprising administering to a patient in need of such treatment an effective amount of a compound of Formula I, or a pharmaceutically acceptable salt thereof. The present invention also provides a method of treating osteoarthritis in a patient, comprising administering to a patient in need of such treatment an effective amount of a compound of Formula I, or a pharmaceutically acceptable salt thereof. In addition, the present invention also provides a method of treating rheumatoid arthritis in a patient, comprising administering to a patient in need of such treatment an effective amount of a compound of Formula I, or a pharmaceutically acceptable salt thereof. The present invention also provides a method of treating pain associated with arthritis in a patient, comprising administering to a patient in need of such treatment an effective amount of a compound of Formula I, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I, or a pharmaceutically acceptable salt thereof. The present invention also provides a method of treating migraine or pain associated with migraine, in a patient, comprising administering to a patient in need of such treatment an effective amount of a compound of Formula I, or a pharmaceutically acceptable salt thereof.

Furthermore, the invention provides a compound of Formula I or a pharmaceutically acceptable salt thereof for use in therapy, in particular for the treatment of osteoarthritis. In addition, the invention provides a compound of Formula I or a pharmaceutically acceptable salt thereof for use in the treatment of rheumatoid arthritis. The invention also provides a compound or pharmaceutically acceptable salt thereof for use in the treatment of pain associated with osteoarthritis or rheumatoid arthritis. Furthermore, the invention provides the use of a compound of Formula I, or a pharmaceutically acceptable salt thereof, for the manufacture of a medicament for the treatment of osteoarthritis. The invention provides the use of a compound of Formula I, or a pharmaceutically acceptable salt thereof, for the manufacture of a medicament for the treatment of rheumatoid arthritis. The present invention also provides the use of a compound of Formula I, or a pharmaceutically acceptable salt thereof, for the manufacture of a medicament for the treatment of pain associated with osteoarthritis or rheumatoid arthritis.

The invention further provides a pharmaceutical composition comprising a compound of Formula I, or a pharmaceutically acceptable salt thereof, in combination with one or more pharmaceutically acceptable carriers, diluents, or excipients. This invention also encompasses novel intermediates and processes for the synthesis of a compound of Formula I, or a pharmaceutically acceptable salt thereof.

In addition, the invention includes a method of treating inflammatory conditions such as arthritis, including osteoarthritis and rheumatoid arthritis, in a patient, comprising administering to a patient in need of such treatment an effective amount of an antagonist of a proinflammatory prostaglandin, such as an EP4 antagonist, in combination with an effective amount of a modulator of a lipoxin or resolvin receptor, such as a modulator of BLT-1, BLT-2, ALX/FPR1, GPR32, CysLT1, CysLT2, or ChemR23.

A further aspect of the invention includes a method of treating inflammatory disease such as arthritis, including osteoarthritis and rheumatoid arthritis, in a patient, comprising administering to a patient in need of such treatment an effective amount of an inhibitor of a proinflammatory prostaglandin synthase, such as an mPGES-1 inhibitor, in combination with an effective amount of a modulator of a lipoxin or resolvin receptor, such as a modulator of BLT-1, BLT-2, ALX/FPR1, GPR32, CysLT1, CysLT2, or ChemR23.

The compounds of the present invention are particularly useful in the treatment methods of the invention. Certain configurations are preferred for compounds of the present invention. The following paragraphs describe such preferred configurations. It will be understood that these preferences are applicable both to the treatment methods and to the compounds of the present invention.

A preferred compound of Formula I is 4-[(1S)-1-[[(2R)-3-methyl-2-(2-phenoxyethoxy)butanoyl]amino]ethyl]benzoic acid:

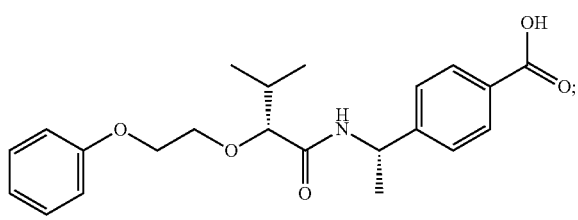 [SMILES: CC(C)[C@@H](OCCOc1ccccc1)C(=O)N[C@@H](C)c1ccc(C(=O)O)cc1]

or a pharmaceutically acceptable salt thereof.

A further preferred compound of Formula I is 4-[(1S)-1-[[(2R)-3-methyl-2-(2-phenoxyethoxy)butanoyl]amino]ethyl]benzoic acid.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I, or pharmaceutically acceptable salts thereof, are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, for example, Remington: The Science and Practice of Pharmacy (D. B. Troy, Editor, 21st Edition, Lippincott, Williams & Wilkins, 2006).

As used herein, "DMEM" refers to Dulbecco's Modified Eagle's Medium; "DMSO" refers to dimethylsulfoxide; "DMF" refers to N,N-dimethylformamide; "THF" refers to tetrahydrofuran; "MeOH" refers to methanol; "EtOAc" refers to ethyl acetate; "PGE$_2$" refers to prostaglandin E$_2$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl]ethanesulfonic acid); "HTRF" refers to homogeneous time-resolved fluorescence technology; "HEK" refers to human embryonic kidney; "HBSS" refers to Hank's Balanced Salt Solution; "EC$_{80}$" refers to the concentration of an agent that produces 80% of the maximal efficacy possible for that agent; and "IC$_{50}$" refers to the concentration of an agent that produces 50% of the maximal inhibitory response possible for that agent.

Pharmaceutically acceptable salts and common methodology for preparing them are well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One skilled in the art of synthesis will appreciate that the compounds of Formula I are readily converted to and may be isolated as a pharmaceutically acceptable salt using techniques and conditions well known to one of ordinary skill in the art.

The compounds of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compounds of Formula I, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

Scheme 1

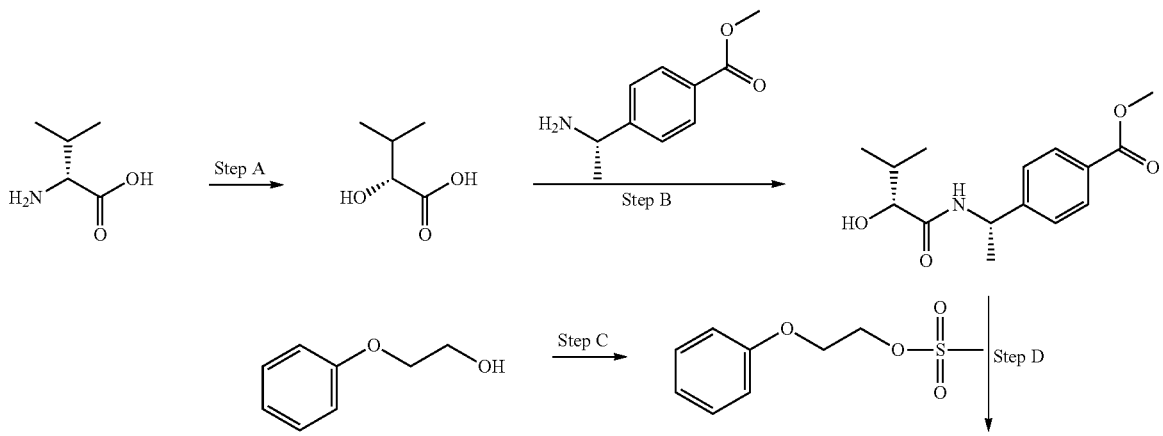

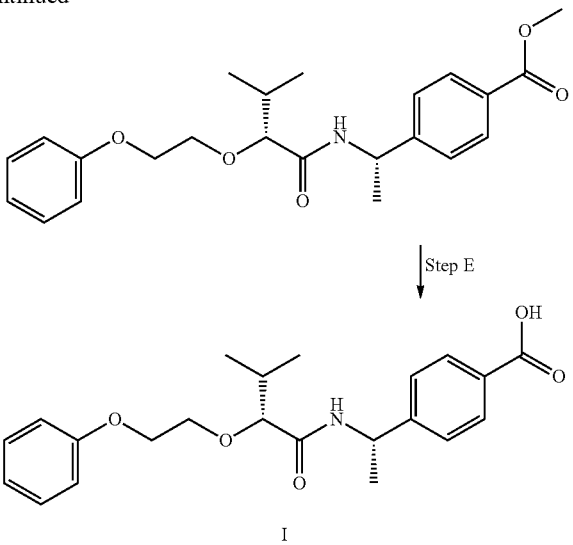

Step E

I

PREPARATION 1

Synthesis of (2R)-2-hydroxy-3-methyl-butanoic acid

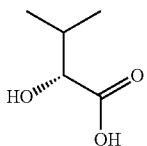

Scheme 1, Step A.

To a solution of water (45 mL) and sulfuric scid (4 mL; 75 mmol) at 0° C. is added D-valine (10 g; 85.4 mmol). To this solution is slowly added a solution of sodium nitrite (8.8 g; 128 mmol) in water (45 mL) over 2 h, keeping the temperature below 5° C. The mixture is allowed to warm slowly to room temperature. After 2 h, the mixture is extracted with diethyl ether (2×75 mL). The combined ether layers are washed with brine, dried (MgSO$_4$), filtered, and concentrated to provide the title compound as a colorless oil (6.1 g, 60%). This material is used in the next step without further purification.

$^1$H NMR (400 MHz, DMSO-d6): δ 12.38 (broad, 1H), 5.02 (broad, 1H), 3.70 (d, J=4.4 Hz, 1H), 1.92-1.85 (m, 1H), 0.86 (d, J=6.9 Hz, 3H), 0.78 (d, J=6.8 Hz, 3H).

PREPARATION 2

Synthesis of methyl 4-[(1S)-1-[[(2R)-2-hydroxy-3-methyl-butanoyl]amino]ethyl]benzoate

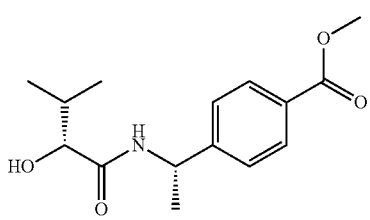 [SMILES: COC(=O)c1ccc([C@H](C)NC(=O)[C@H](O)C(C)C)cc1]

Scheme 1, Step B.

A mixture of 4-[(1S)-1-aminoethyl]-benzoic acid, methyl ester (5.8 g; 49.1 mmol), (2R)-2-hydroxy-3-methyl-butanoic acid (9.3 g; 51.9 mmol), 1-hydroxybenzotriazole (0.82 g; 6.1 mmol), and triethylamine (22 mL; 158 mmol) in CH$_2$Cl$_2$ (120 mL) is treated with 1-(3-dimethylaminopropyl)-3-ethylcarbodiimide hydrochloride (14.2 g; 74.1 mmol). The cloudy mixture is stirred at room temperature overnight. The reaction mixture is washed with 1N HCl (2×150 mL) then brine. The organic layer is dried over MgSO$_4$, filtered, concentrated, and dried under high vacuum to provide the title compound as a white solid (10.24 g, 75%). This material is used in the next step without further purification. MS (m/z): 280.0 (M+1).

$^1$H NMR (400 MHz, DMSO-d6): δ 8.14-8.12 (m, 1H), 7.87-7.84 (m, 2H), 7.45-7.43 (m, 2H), 5.35 (d, J=5.7 Hz, 1H), 5.00-4.95 (m, 1H), 3.79 (s, 3H), 3.64 (dd, J=4.0, 5.7 Hz, 1H), 1.93-1.89 (m, 1H), 1.36 (d, J=7.2 Hz, 3H), 0.81 (d, J=6.9 Hz, 3H), 0.65 (d, J=6.7 Hz, 3H).

PREPARATION 3

Synthesis of 2-phenoxyethyl methanesulfonate

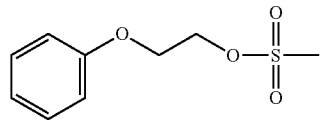

Scheme 1, Step C.

To a solution of 2-phenoxyethanol (10.0 mL, 80.0 mmol) and triethylamine (13.5 mL, 96.9 mmol) in anhydrous CH$_2$Cl$_2$ (250 mL) at 0° C. is added methanesulfonyl chloride (6.80 mL, 87.9 mmol). The resulting cloudy mixture is stirred at 0° C. for 2 h. The mixture is diluted with water (75 mL) and extracted. The organic layer is washed with 1N HCl (75 mL) then saturated NaHCO$_3$/brine (1:1; 75 mL) dried (Na$_2$SO$_4$), filtered, and concentrated. The residue is dried to constant weight under reduced pressure to provide the title compound as a pale yellow oil (17.1 g, 99%). This material is used in the next step without further purification.

$^1$H NMR (400 MHz, CDCl$_3$): δ 7.31-7.27 (m, 2H), 7.01-6.96 (m, 1H), 6.91-6.87 (m, 2H), 4.58-4.55 (m, 2H), 4.24-4.22 (m, 2H), 3.08 (s, 3H).

PREPARATION 4

Synthesis of methyl 4-[(1S)-1-[[(2R)-3-methyl-2-(2-phenoxyethoxy)butanoyl]amino]ethyl]benzoate

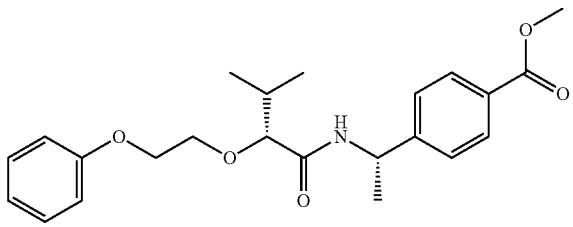 [SMILES: COC(=O)c1ccc([C@H](C)NC(=O)[C@H](OCCOc2ccccc2)C(C)C)cc1]

Scheme 1, Step D.

To a solution of methyl 4-[(1S)-1-[[(2R)-2-hydroxy-3-methyl-butanoyl]amino]ethyl]benzoate (3.0 g, 10.7 mmol) and 2-phenoxyethyl methanesulfonate (2.32 g, 10.7 mmol) in dry THF (25 mL) is added sodium hydride (440 mg, 10.7 mmol). The mixture is stirred at room temperature overnight and partitioned between 1N HCl and EtOAc. The aqueous layer is extracted with EtOAc. The combined EtOAc layers are washed with brine, dried with MgSO$_4$, filtered, and concentrated. The crude material (4.7 g) is purified using silica gel column chromatography (120 g cartridge; 30 to 100% ethyl acetate in heptane) to provide the title compound as a white solid (1.41 g, 33%). MS (m/z): 400.2 (M+1).

$^1$H NMR (400 MHz, DMSO-d6): δ 8.21-8.18 (m, 1H), 7.87-7.84 (m, 2H), 7.43-7.41 (m, 2H), 7.26-7.22 (m, 2H), 6.91-6.87 (m, 3H), 5.01-4.97 (m, 1H), 4.10-4.07 (m, 2H), 3.79 (s, 3H), 3.78-3.74 (m, 1H), 3.70-3.65 (m, 1H), 3.52 (d, J=5.5 Hz, 1H), 1.95-1.92 (m, 1H), 1.32-1.30 (m, 3H), 0.82-0.79 (m, 3H), 0.75 (d, J=6.7 Hz, 3H).

EXAMPLE 1

Synthesis of 4-[(1S)-1-[[(2R)-3-methyl-2-(2-phenoxyethoxy)butanoyl]amino]ethyl]benzoic acid

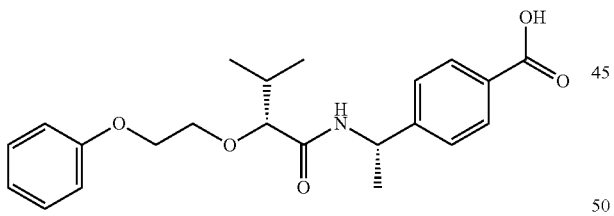

Scheme 1, Step E.

To a solution of methyl 4-[(1S)-1-[[(2R)-3-methyl-2-(2-phenoxyethoxy)butanoyl]amino]ethyl]benzoate (2.0 g, 5.01 mmol) in MeOH (25 mL) and THF (25 mL) is added 5N NaOH (10 mL, 50 mmol). The mixture is stirred at room temperature for 1.5 h, treated with 5N HCl (10 mL), and concentrated to remove organic solvents. The aqueous residue is extracted with ethyl acetate (3×30 mL). The combined ethyl acetate layers are dried with MgSO$_4$, filtered, and concentrated. The crude material (1.36 g) is dissolved in ethyl acetate and washed with 1N NaOH (25 mL). The aqueous layer is extracted with ethyl acetate (25 mL), acidified with 1N HCl (25 mL), and extracted with ethyl acetate (3×25 mL). The combined ethyl acetate layers are dried with MgSO$_4$, filtered, and concentrated to a waxy solid. This material is co-evaporated with MeOH (3×) to provide the title compound as a white solid (925 mg, 48%). MS (m/z): 386.2 (M+1).

$^1$H NMR (400 MHz, DMSO-d6): δ 12.82 (broad), 8.17-8.15 (m, 1H), 7.85-7.82 (m, 2H), 7.39 (d, J=8.3 Hz, 2H), 7.26-7.22 (m, 2H), 6.91-6.87 (m, 3H), 5.01-4.98 (m, 1H), 4.09 (t, J=4.6 Hz, 2H), 3.80-3.76 (m, 1H), 3.69-3.65 (m, 1H), 3.53 (d, J=5.5 Hz, 1H), 1.96-1.93 (m, 1H), 1.31 (d, J=7.1 Hz, 3H), 0.80 (d, J=6.8 Hz, 3H), 0.76 (d, J=6.7 Hz, 3H).

Scheme 2

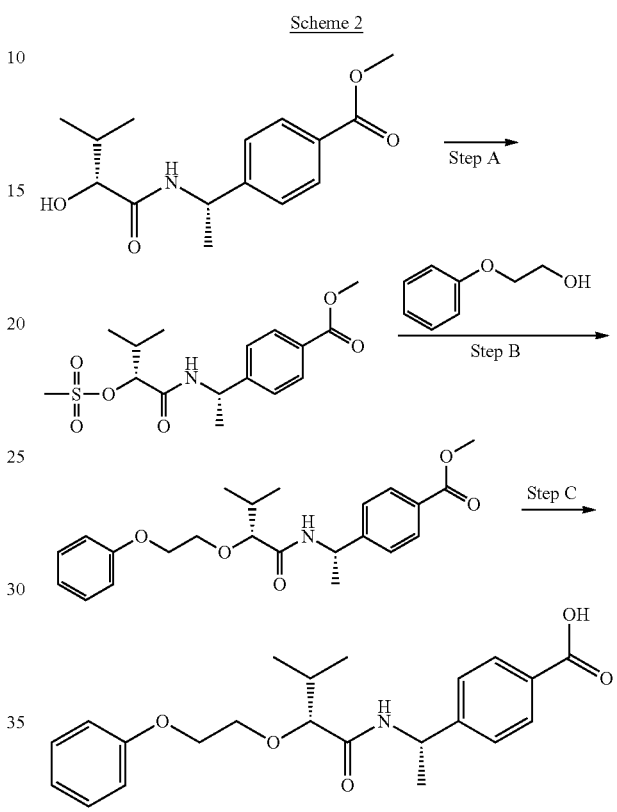

PREPARATION 5

Synthesis of methyl 4-[(1S)-1-[[(2R)-3-methyl-2-methylsulfonyloxy-butanoyl]amino]ethyl]benzoate

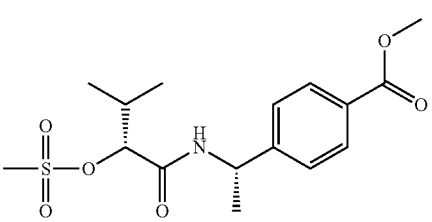

Scheme 2, Step A.

A mixture of methyl 4-[(1S)-1-[[(2R)-2-hydroxy-3-methyl-butanoyl]amino]ethyl]benzoate (40 g; 143 mmol), and triethylamine (22.0 mL, 157 mmol) in CH$_2$Cl$_2$ (400 mL) is cooled to 0° C. A solution of methanesulfonyl chloride (11.1 mL, 143 mmol) in CH$_2$Cl$_2$ (200 mL) is added dropwise over 45 min, and the mixture is stirred to room temperature for 1 h. The mixture is washed sequentially with 1N HCl (100 mL) and aq. NaHCO$_3$ (200 mL). The organic layer is dried over MgSO$_4$, filtered, and concentrated. The crude material is slurried in methyl t-butyl ether (200 mL) and hexane (600 mL) for 30 min, filtered, and dried under vacuum to provide the title compound as a white solid (50 g, 98%). MS (m/z): 358.2 (M+1).
$^{1}$H NMR (400 MHz, DMSO-d6): δ 8.74 (d, J=8.0 Hz, 1H), 7.92 (d, J=8.0 Hz, 2H), 7.49 (d, J=8.5 Hz, 2H), 5.07-4.97 (m, 1H), 4.64 (d, J=5.8 Hz, 1H), 3.84 (s, 3H), 3.14 (s, 3H), 2.17-2.06 (m, 1H), 1.40 (d, J=7.1 Hz, 3H), 0.92-0.86 (m, 6H).

PREPARATION 6

Synthesis of methyl 4-[(1S)-1-[[(2R)-3-methyl-2-(2-phenoxyethoxy)butanoyl]amino]ethyl]benzoate

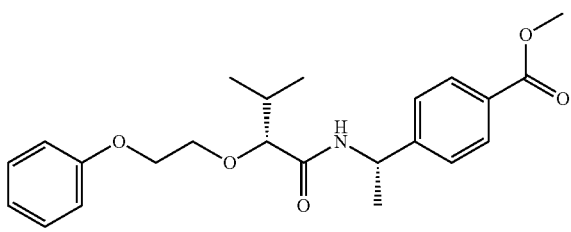 [SMILES: COC(=O)c1ccc([C@H](C)NC(=O)[C@H](OCCOc2ccccc2)C(C)C)cc1]

Scheme 2, Step B.

Under a nitrogen atmosphere, 2-phenoxyethanol (17.3 mL, 138 mmol) in THF (450 mL) is cooled to 5° C. using an ice water bath and treated dropwise over 5 min with a 1M solution of potassium tert-butoxide in THF (138 mL, 138 mmol). The mixture is stirred for 30 min, and methyl 4-[(1S)-1-[[(2R)-3-methyl-2-methylsulfonyloxy-butanoyl]amino]ethyl]benzoate (45 g, 126 mmol) is added in one portion. The mixture is stirred to room temperature for 1 h, and water (300 mL) is added. The layers are separated, and the aqueous layer is extracted with ethyl acetate (100 mL). The combined organic layers are washed with brine, dried over MgSO$_4$, filtered, and concentrated. The crude material is purified using silica gel column chromatography (750 g cartridge; 20 to 60% ethyl acetate in heptane) to provide the title compound as a white solid (30 g, 60%). MS (m/z): 400.4 (M+1).

ALTERNATIVE SYNTHESIS OF EXAMPLE 1

Alternative synthesis of 4-[(1S)-1-[[(2R)-3-methyl-2-(2-phenoxyethoxy)butanoyl]amino]ethyl]benzoic acid

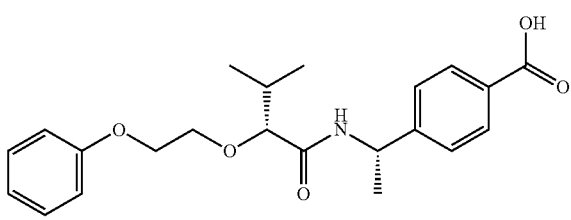 [SMILES: CC(C)[C@@H](OCCOc1ccccc1)C(=O)N[C@@H](C)c1ccc(C(=O)O)cc1]

Scheme 2, Step C.

To a solution of methyl 4-[(1S)-1-[[(2R)-3-methyl-2-(2-phenoxyethoxy)butanoyl]amino]ethyl]benzoate (30 g, 75.1 mmol) in THF (300 mL) is added 2N NaOH (94 mL, 188 mmol). The mixture is stirred at 55° C. overnight, cooled, and concentrated to remove THF. The aqueous residue is diluted with water (200 mL) and extracted with ethyl acetate (2×200 mL). The organic layers are discarded. The aqueous layer is acidified to pH 2 using conc. HCl (25 mL) and extracted with ethyl acetate (2×200 mL). The combined ethyl acetate layers are dried with MgSO$_4$, filtered, and concentrated. The material is slurried with heptane (500 mL) at 60° C. for 2 h, cooled to room temperature, and filtered. The resulting solid is slurried with water (500 mL) at 60° C. for 2 h, cooled to room temperature, filtered, and dried at 40° C. to provide the title compound as a white solid (20 g, 69%). MS (m/z): 386.0 (M+1).

X-Ray Powder Diffraction (XRPD) of 4-[(1S)-1-[[(2R)-3-methyl-2-(2-phenoxyethoxy)butanoyl]amino]ethyl]benzoic acid The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U.S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

Crystal Preparation of form 1 of 4-[(1S)-1-[[(2R)-3-methyl-2-(2-phenoxyethoxy)butanoyl]amino]ethyl]benzoic acid Suspend 4-[(1S)-1-[[(2R)-3-methyl-2-(2-phenoxyethoxy)butanoyl]amino]ethyl]benzoic acid (4 g) in heptanes (120 mL), and stir for 1 hour at 80° C. Cool the mixture to ambient temperature, collect the solids by filtration, and dry the solids under vacuum to provide 3 g (75% yield) of 4-[(1S)-1-[[(2R)-3-methyl-2-(2-phenoxyethoxy)butanoyl]amino]ethyl]benzoic acid, form 1.

TABLE 1

X-ray powder diffraction peaks of 4-[(1S)-1-[[(2R)-3-methyl-2-(2-phenoxyethoxy)butanoyl]amino]ethyl] benzoic acid, form 1.

| Peak | Angle (2-Theta °) | Intensity (%) |
| --- | --- | --- |
| 1 | 8.62 | 100 |
| 2 | 12.32 | 21 |
| 3 | 12.68 | 14 |
| 4 | 13.81 | 20 |
| 5 | 14.67 | 54 |
| 6 | 14.91 | 17 |

TABLE 1-continued

X-ray powder diffraction peaks of 4-[(1S)-1-[[(2R)-3-methyl-2-(2-phenoxyethoxy)butanoyl]amino]ethyl]benzoic acid, form 1.

| Peak | Angle (2-Theta °) | Intensity (%) |
|------|-------------------|---------------|
| 7    | 17.10             | 15            |
| 8    | 17.58             | 68            |
| 9    | 17.79             | 37            |
| 10   | 20.02             | 15            |
| 11   | 20.96             | 9             |
| 12   | 21.71             | 17            |
| 13   | 23.10             | 22            |
| 14   | 23.56             | 61            |
| 15   | 24.01             | 16            |
| 16   | 24.78             | 17            |
| 17   | 25.51             | 41            |
| 18   | 25.89             | 12            |
| 19   | 31.60             | 7             |

In Vitro Binding to Human EP1, EP2, EP3 and EP4 hEP1 and hEP4 membranes are prepared from recombinant HEK293 cells stably expressing the human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

$K_d$ values for $^3$H-PGE$_2$ binding to each receptor are determined by saturation binding studies or homologous competition. Compounds are tested in a 96-well format using a three-fold dilution series to generate a 10-point curve. Diluted compound is incubated with 20 μg/well EP1, 10 μg/well EP2, 1 ug/well EP3 or 10 to 20 μg/well EP4 membrane for 90 minutes at 25° C. in the presence of 0.3 to 0.5 nM [$^3$H]-PGE$_2$ (PerkinElmer, 118 to 180 Ci/mmol). The binding reaction is performed in 200 μL MES buffer (10 mM MES pH 6.0 with KOH, 10 mM MgCl$_2$ and 1 mM EDTA) using 0.5 mL polystyrene 96-well deep-well plates. Nonspecific binding is calculated by comparing binding in the presence and absence of 2 μM of PGE$_2$. The membranes are harvested by filtration (TomTek harvester), washed 4 times with cold buffer (10 mM MES pH 6.0 with KOH, 10 mM MgCl$_2$), dried in a 60° C. oven, and the radioactivity is quantified as counts per minute (CPM) using a TopCount detector. Percent specific binding is calculated as the percent of the binding in the absence of any inhibitor, corrected for binding in the presence of 2 μM of PGE$_2$. Data are analyzed using a 4-parameter nonlinear logistic equation (ABase Equation 205) as shown: $y=(A+((B-A)/(1+((C/x)^D))))$ where, y=% specific inhibition, A=bottom of the curve; B=top of the curve; C=relative IC$_{50}$=concentration causing 50% inhibition based on the range of the data from top to bottom; D=Hill Slope=slope of the curve. $K_i$ conversion from IC$_{50}$ Values ($K_i=IC_{50}/(1+[L]/K_d)$) where [L] is the ligand concentration).

TABLE 2

In vitro binding of Example 1 to human EP1, EP2, EP3 and EP4

| Test Compound | hEP1, K$_i$ (nM) | hEP2, K$_i$ (nM) | hEP3, K$_i$ (nM) | hEP4, K$_i$ (nM) |
|---------------|------------------|------------------|------------------|------------------|
| Example 1     | >17400 (n = 1)   | 261 ± 108 (n = 2) | >12700 (n = 1)  | 0.45 ± 0.26 (n = 3) |

Following the procedures essentially as described above, the data in Table 2 demonstrate that the compound of Example 1 binds to hEP4 at low nanomolar concentrations. The data in Table 2 also demonstrate the compound of Example 1 binds to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 μg/mL geneticin and 2 mM L-glutamine. Confluent cultures are grown at 37° C. in an atmosphere containing 5% CO$_2$. Cells are harvested using 2.5% Trypsin-EDTA, suspended in freeze media (FBS with 6% DMSO) at 10$^7$ cells/mL and aliquots are stored in liquid nitrogen. Just before assay, cells are thawed in DMEM, centrifuged, and resuspended in cAMP buffer.

The inhibition of PGE$_2$-stimulated cAMP production by EP4 antagonists is measured using HTRF (Cisbio catalogue #62AM4PEB). An aliquot equivalent to 4000 cells is incubated with 50 μL cAMP assay buffer containing PGE$_2$ in a concentration predetermined to produce an EC$_{80}$ (0.188 nM PGE$_2$ from Sigma, catalog # P5640-10 mg) and EP4 antagonists at room temperature for 20 minutes. cAMP assay buffer contains 500 mL HBSS, 0.1% BSA, 20 mM HEPES and 200 μM IBMX (Sigma 15879). CJ-042794 serves as a positive control (see WO 2005/021508, example 68, 4-{(1S)-1-[({5-chloro-2-[(4-fluorophenyl)oxy]phenyl}carbonyl)amino]ethyl}benzoic acid; see also Murase, A., et al., Life Sciences, 82:226-232 (2008)). To measure the cAMP levels, cAMP-d2 conjugate and anti cAMP-cryptate conjugate in lysis buffer are incubated with the treated cells at room temperature for 1 hour. The HTRF signal is detected using an EnVision® plate reader (Perkin-Elmer) to calculate the ratio of fluorescence at 665 nm to that at 620 nm. The raw data are converted to cAMP amount (pmol/well) using a cAMP standard curve generated for each experiment. Data are analyzed using a 4-parameter nonlinear logistic equation (ABase Equation 205) as shown: $y=(A+((B-A)/(1+((C/x)^D))))$ where, y=% specific inhibition, A=Bottom of the curve, B=Top of the curve, C=Relative IC$_{50}$=concentration causing 50% inhibition based on the range of the data from top to bottom, D=Hill, Slope=slope of the curve.

Following the procedures essentially as described above, the compound of Example 1 has an IC$_{50}$ of 2.2±1.7 nM (n=5) measured at human EP4. This demonstrates that the compound of Example 1 is a potent antagonist of human EP4 in vitro.

In Vitro Rat EP4 Functional Antagonist Activity

Rat EP4 cDNA (Genebank Accession# NM_03276) is cloned into pcDNA 3.1 vector and subsequently transfected in HEK293 cells for receptor expression. Rat EP4 stable clone is scaled up and then frozen down as cell bank for future compounds screening. To test EP4 antagonist compounds in rEP4 cells, thaw the frozen cells and then resuspend cells in cAMP assay buffer. The cAMP buffer is made by HBSS without Phenol Red (Hyclone, SH30268) supplemented with 20 mM HEPES (Hyclone, SH30237), 0.1% BSA (Gibco, 15260) and 125 μM IBMX (Sigma, 15879). The cells are plated into 96-well half area flat-bottom polystyrene black plates (Costar 3694). Compounds are serial diluted with DMSO to give 10-point concentration response curves. Then diluted compounds are added into cAMP assay buffer which contains $PGE_2$ (Cayman 14010, in a concentration predetermined to produce an $EC_{80}$) at ratio of DMSO/buffer at 1/100. The cells are treated with compounds in the presence of $PGE_2$ ($EC_{80}$ concentration) for 30 minutes at room temperature. The cAMP levels generated from the cells are quantified by a cAMP HTRF assay kit (Cisbio 62AM4PEC). The plates are read on an EnVision plate reader using HTRF optimized protocol (PerkinElmer). $IC_{50}$s are calculated using Graphpad Prism (v. 4) nonlinear regression, sigmoidal dose response curve fitting.

Following the procedures essentially as described above, the compound of Example 1 has an $IC_{50}$ of 2.0 nM (n=1) measured at rat EP4. This demonstrates that the compound of Example 1 is a potent antagonist of rat EP4 in vitro.

In Vitro Antagonist Activity in Human Whole Blood

The inhibitory effects of $PGE_2$ on LPS-induced TNFα production from macrophages/monocytes are believed to be mediated by EP4 receptors (See Murase, A., et al., *Life Sciences*, 82:226-232 (2008)). The ability of the compound of Example 1 to reverse the inhibitory effect of $PGE_2$ on LPS-induced TNFα production in human whole blood is an indicia of functional activity.

Blood is collected from normal volunteer donors into sodium heparin vacutainer tubes. Donors have not taken NSAIDs or celecoxib within 48 hours or glucocorticoids within two weeks prior to the donation. All tubes/donor are pooled into 50 mL Falcon conical centrifuge tubes and 98 μL/well is distributed into 96-well tissue culture plates (Falcon 3072). Compounds are diluted into DMSO to 100× final and 1 μL/well in triplicate is added to the blood to give 7-point concentration response curves. The blood is pretreated with the compounds at 37° C., in a 5% $CO_2$ humidified atmosphere, for 30 minutes, after which 1 μL/well of a solution of 1 mg/mL of lipopolysaccharide (LPS) (Sigma 0111:B4) in 0.2 mg/mL bovine serum albumin (BSA)/PBS both with and without 1 mM $PGE_2$ (Cayman 14010) is added to give a final LPS concentration of 10 μg/mL both with and without 10 nM $PGE_2$. The plates are incubated for 20-24 hours at 37° C. in a 5% $CO_2$, humidified atmosphere. The plates are centrifuged at 1800×g for 10 minutes at 22° C., in an Eppendorf 5810R centrifuge. Plasma is removed from the cell layer and is transferred to v-bottom polypropylene plates. TNFα levels in 2 μL plasma are quantified by a commercially available enzyme immunoassay (R&D Systems DY210), using Immulon 4 HBX plates (Thermo 3855) and 3,3',5,5' tetramethylbiphenyl-4,4'-diamine substrate (KPL 50-76-03). The plates are read at $A_{450}$-$A_{650}$ on a plate reader (Molecular Devices Versamax) using SOFTmaxPRO (v. 4.3.1) software. $IC_{50}$s are calculated using Graphpad Prism (v. 4) nonlinear regression, with sigmoidal dose response curve fitting. Results are expressed as the geometric mean±standard deviation; n=number of independent determinations.

Following the procedures essentially as described above, the compound of Example 1 has an $IC_{50}$ of 20±24 nM (n=11) measured at human EP4. This demonstrates that the compound of Example 1 is a potent EP4 antagonist in the human blood TNFα induction assay.

We claim:

1. A compound of the formula:

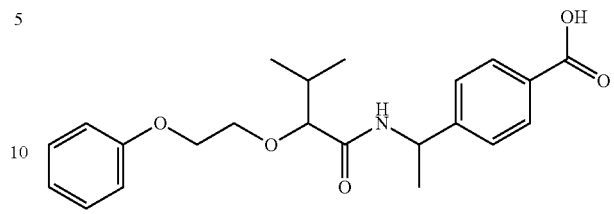

or a pharmaceutically acceptable salt thereof.

2. The compound according to claim 1 which is:

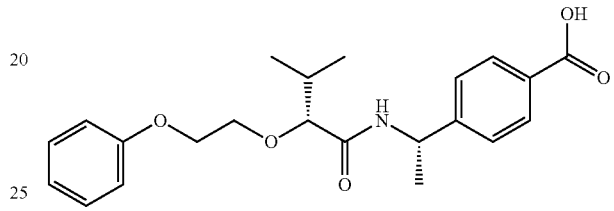

or a pharmaceutically acceptable salt thereof.

3. The compound according to claim 2 which is:

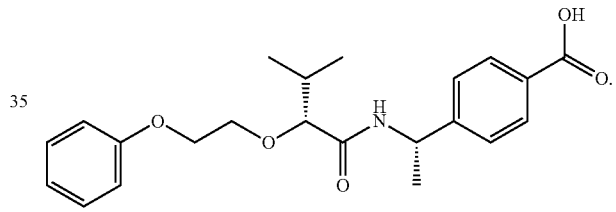

4. A method of treating osteoarthritis in a patient, comprising administering to a patient in need of such treatment an effective amount of a compound, or pharmaceutically acceptable salt thereof, of claim 1.

5. A method of treating rheumatoid arthritis in a patient, comprising administering to a patient in need of such treatment an effective amount of a compound or pharmaceutically acceptable salt thereof, of claim 1.

6. A method of treating pain associated with osteoarthritis in a patient, comprising administering to a patient in need of such treatment an effective amount of a compound or a pharmaceutically acceptable salt thereof, of claim 1.

7. A method of treating pain associated with rheumatoid arthritis in a patient, comprising administering to a patient in need of such treatment an effective amount of a compound or a pharmaceutically acceptable salt thereof, of claim 1.

8. A pharmaceutical composition, comprising a compound or a pharmaceutically acceptable salt thereof of claim 1 in combination with one or more pharmaceutically acceptable carriers, diluents, or excipients.

* * * * *